United States Patent [19]
Nakanishi et al.

[11] Patent Number: 5,989,874
[45] Date of Patent: *Nov. 23, 1999

[54] HUMECTANT, ANTISTATIC AGENT, DISPERSANT AND FILM-FORMING AGENT HAVING POLYSACCHARIDE AS ACTIVE PRINCIPLE, PREPARATION PROCESS OF POLYSACCHARIDES, AND *KLIEBSIELLA OCYTOCA* TNM-3 STRAIN

[75] Inventors: Osamu Nakanishi, Ibaraki; Yoichi Ooiso, Higashiosaka; Takeshi Okumiya, Yao; Ryosuke Sugihara, Osaka; Kaoru Kawashima, Habikino, all of Japan

[73] Assignee: Tayca Corporation, Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/620,285

[22] Filed: Mar. 22, 1996

[30] Foreign Application Priority Data

| Mar. 27, 1995 | [JP] | Japan | 7-093100 |
|---|---|---|---|
| May 1, 1995 | [JP] | Japan | 7-131040 |
| Jun. 28, 1995 | [JP] | Japan | 7-184738 |
| Jul. 4, 1995 | [JP] | Japan | 7-191280 |
| Jul. 18, 1995 | [JP] | Japan | 7-203845 |

[51] Int. Cl.$^6$ .................. C12P 19/04; C12N 1/20
[52] U.S. Cl. .............. 435/101; 435/72; 435/252.1; 435/852; 536/123
[58] Field of Search ............. 435/72, 101, 852, 435/252.1; 536/123

[56] References Cited

U.S. PATENT DOCUMENTS

| 4,514,563 | 4/1985 | Fujiyama et al. | 536/123 |
|---|---|---|---|
| 4,806,636 | 2/1989 | Harris et al. | 536/123 |
| 4,906,746 | 3/1990 | Barnier et al. | 536/127 |
| 4,921,793 | 5/1990 | Rosenberg et al. | 435/84 |
| 4,950,604 | 8/1990 | Graber-Gubert et al. | 435/252.1 |
| 4,975,371 | 12/1990 | Kawaguchi | 435/101 |
| 5,476,656 | 12/1995 | Kawaguchi et al. | 424/116 |

FOREIGN PATENT DOCUMENTS

| 0 379 999 | 8/1990 | European Pat. Off. . |
|---|---|---|
| 0 618 232 A2 | 10/1994 | European Pat. Off. . |
| 2 058 107 | 4/1981 | United Kingdom . |

OTHER PUBLICATIONS

The ATCC Catalogue of Bacteria and Bacteriophages, 18th ed., p. 165, 1992.
Beurret et al. Carbohydrate Res. vol. 157 1986 pp. 13–25.
Patent Abstracts of Japan vol. 018, No. 433 (C–1239) Aug. 18, 1994 corresponding to JP 06 136003.

*Primary Examiner*—Leon B. Lankford, Jr.
*Assistant Examiner*—Christopher R. Tate
*Attorney, Agent, or Firm*—David G. Conlin; Christine C. O'Day

[57] ABSTRACT

The disclosure describes a humectant, antistatic agent, film-forming agent or dispersant comprising an effective amount of a polysaccharide produced by two strains of Kliebsiella composed of D-glucuronic acid, L-rhamnose, D-galactose and D-glucose in a molar ratio of D-glucuronic acid:L-rhamnose:D-galactose:D-glucose = 0.8–1.2:2.4–3.6:0.8–1.2:0.8–1.2.

4 Claims, 1 Drawing Sheet

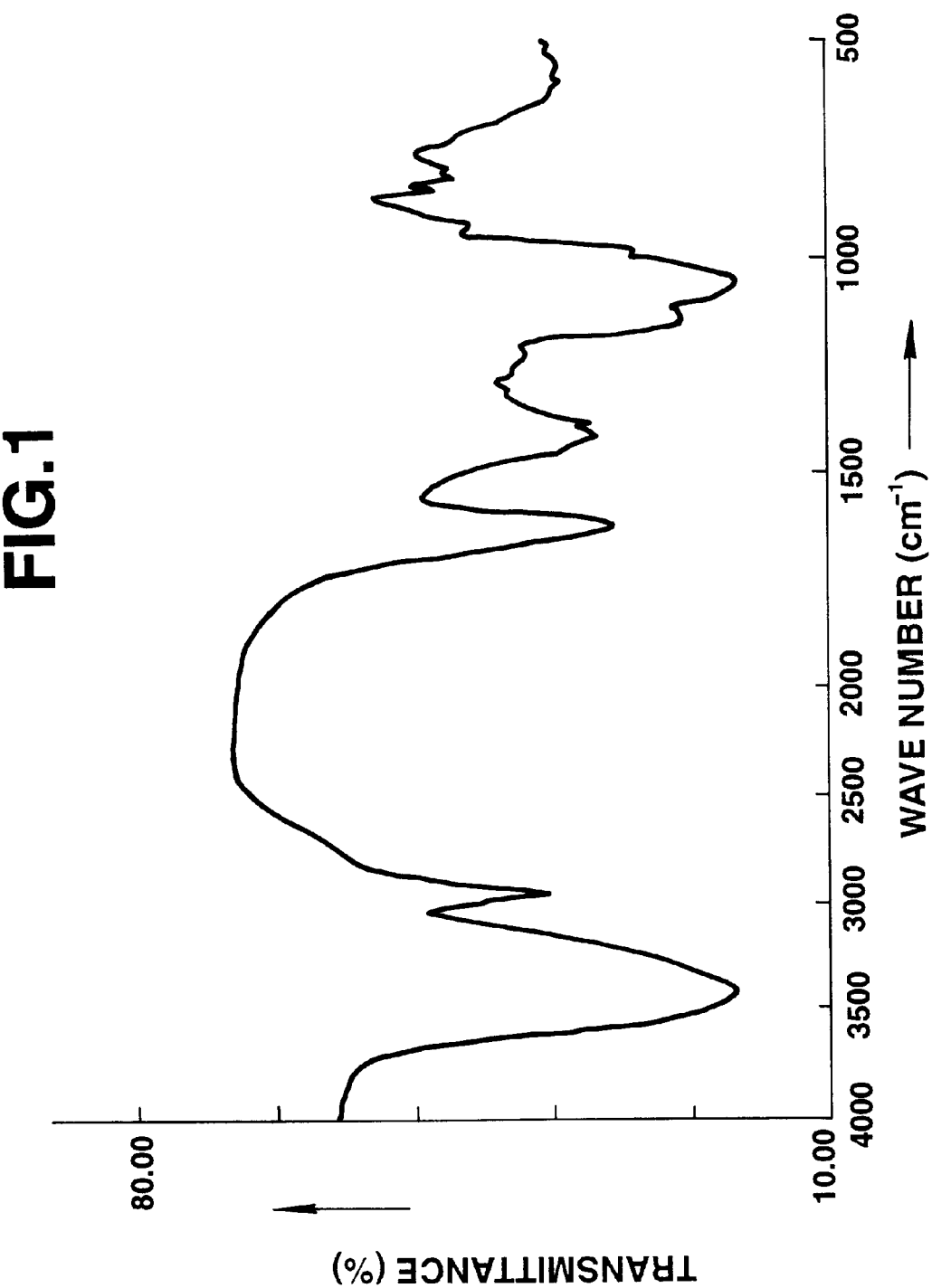

HUMECTANT, ANTISTATIC AGENT, DISPERSANT AND FILM-FORMING AGENT HAVING POLYSACCHARIDE AS ACTIVE PRINCIPLE, PREPARATION PROCESS OF POLYSACCHARIDES, AND *KLIEBSIELLA OCYTOCA* TNM-3 STRAIN

BACKGROUND OF THE INVENTION

The present invention relates to a humectant, antistatic agent, dispersant and film-forming agent containing a polysaccharide as active principle, a preparation process of polysaccharides, and *Kliebsiella oxytoca* TNM-3 strain. More particularly, it relates to a tyrosinase-inhibitory humectant containing a polysaccharide as active principle, and cosmetic compositions containing said humectant; an antistatic agent containing a polysaccharide with high biodegradability as active principle; a dispersant containing a polysaccharide as active principle and capable of dispersing, to inorganic and oleaginous substances in a quite satisfactory way; a film-forming agent containing a polysaccharide as active principle, which is capable of forming a low-viscosity solution and can contain an antibacterial metal as counter ion, and films having high break elongation property formed by using said film-forming agent; a preparation process of polysaccharides; and polysaccharide-productive *Kliebsiella oxytoca* TNM-3 strain.

Generally, hyaluronic acid and chitosan have been used as humectant. For instance, Japanese Patent Application Laid-Open (KOKAI) No. 63-156707 discloses a cosmetic composition containing hyaluronic acid having a molecular weight of not less than 2,000,000 as humectant. This humectant is disclosed as having the effect of protecting the skin against the outside stimulus and preventing skin chapping and also contributory to bettering the feeling of use of the cosmetics.

In use of humectant as a cosmetic material, it is required that such humectant has a moisture retention percentage preferably in a range of 10 to 50% under the ordinary environmental conditions with a relative humidity of 40–80%. Such humectant is also required that its moisture retaining ability should be scarcely affected by the change of relative humidity (See Fragrance Journal, special issue No. 9 "Science of Humectant", 1988, pp. 34, etc.).

Kojic acid and arbutin are also known to have a tyrosinase-inhibitory activity and blended in the cosmetic composition as a skin beautifying agent.

However, the humectant comprising hyaluronic acid as a primary principle has the serious defect that its moisture retainability is not stable because it changes depending on the ambient humidity.

Glycerol and sodium pyrrolidonecarboxylate as humactant have also the same defect as hyaluronic acid mentioned above, and further their moisture retention is low under the low humidity conditions, so that their effect is not satisfactory in an environment where the humectant is required to exhibit its maximum performance. Also, because of too high hygroscopicity under the high-humidity conditions like the effect with hyaluronic acid, these humectants may serve for giving a sense of stickiness to the skin of the user of the cosmetics or may rather act to deprive the user's skin moisture.

The humectants comprising chitosan also have the serious defect that their moisture retaining performance is low under a low-humidity condition where high moisture retention is required.

No humectant is known which is credited with tyrosinase-inhibitory activity among the conventional humectants such as hyaluronic acid. On the other hand, a significant moisture retainability is not observed in the conventional skin-beautifying agents such as kojic acid and arbutin.

Antistatic agents, in practical use thereof, are applied on the surfaces of plastic articles or synthetic fibers or incorporated in the materials thereof. However, when a low-molecular weight surfactant is used as antistatic agent, its effect will not last long since it may be easily wiped out with a cloth or washed away.

In view of the above, it is remarkable to the synthetic polymer type antistatic agents such as polyethylene glycol, polyoxyethylenediamine, polyvinylbenzyltrimethylammonium chloride, polydiallyldimethylammonium chloride, sodium polystyrenesulfonate and the like which are capable of keeping effect permanently. However, considering the recently environmental pollution problems, it is pointed out that these polymeric antistatic agents are quite unsatisfactory to biodegradability and safety because of synthetic polymer.

Various types of polysaccharides, which are high-molecular weight compounds, such as dextran, pullulan, curdlan, xanthan gum, gellan gum, hyaluronic acid, etc., are utilized in the fields of medicine, foodstuff, cosmetics, etc. Since these polysaccharides are natural products, they have high safety characteristics, and further since they are biodegradable, the scope of their use is expanding as a material which is well compatible with the global environment and the living things.

Natural polysaccharides can be roughly divided into the three types: those derived from plants, those derived from animals and those derived from microorganisms. Among them, those derived from microorganisms, or so-called microorganism-produced polysaccharides are remarkable from the aspects of supply and productivity, and several studies are under way (such as disclosed in Japanese Patent Application Laid-Open (KOKAI) No. 6-136003). Regarding use for dispersants, xanthan gum, which is a microorganism-produced polysaccharide, is widely utilized in many fields of industry.

The dispersants using xanthan gum as a primary ingredient are poor in dispersibility for the inorganic and oleaginous substances, so that a polysaccharide having better dispersibility for above substances is demanded in the market.

Regarding use of film-forming agents, pullulan, which is microorganism-produced polysaccharide, is widely used in many fields of industry. Xanthan gum and hyaluronic acid are also known to have film-forming properties.

However, the films made by using pullulan has low bleak elongation property. Also, since pullulan is a neutral polysaccharide, it is incapable of containing an antibacterial metal such as silver, copper, zinc, etc., as counter ion of acidic polysaccharides. Therefore it is impossible to produce an antibacterial film from pullulan alone.

Generally, for efficient production of films, it is advantageous to the cost down of film-forming that the film-forming agent is used at the high concentrated solution so as to minimize the amount of water evaporated. However, in the case of the acidic polysaccharides such as xanthan gum and hyaluronic acid which are capable of producing the antibacterial film, it is very difficult to prepare the film at a highly concentrated solution because of extremely high viscosity of the solution of these polysaccharides, so that these polysaccharides are unfavorable for the film-forming agents.

In production of polysaccharides by use of microorganisms, it is desirable to use a microorganism having an extracellular polysaccharide productivity, considering ease of collection and purification of the produced polysaccharide.

As a result of the present inventor's earnest studies, it has been found that certain specific polysaccharides produced by a bacterium belonging to the genus Kliebsiella (1) have a tyrosinase-inhibitory activity in addition to a stabilized moisture retainability and are especially suited for blending in cosmetics; (2) have excellent antistatic properties; (3) have excellent dispersibility for the inorganic and oleaginous substances; and (4) are capable of forming a low-viscosity aqueous solution, can contain an antibacterial metal as counter ion and can form a film having high break elongation property. The present invention has been attained on the basis of these findings.

SUMMARY OF THE INVENTION

An object of the present invention is to provide a humectant comprising polysaccharides as active principle and having high moisture retainability and a tyrosinase-inhibitory activity, and cosmetic compositions containing the said humectant.

Another object of the present invention is to provide an antistatic agent having a more excellent biodegradability and higher safety than the synthetic polymer type antistatic agents.

Still another object of the present invention is to provide a dispersant having an excellent dispersibility for the inorganic and oleaginous substances.

Yet another object of the present invention is to provide a film-forming agent whose aqueous solution has low viscosity, and which is capable of forming a film having high break elongation property and can also contain an antibacterial metal as counter ion stably.

A further object of the present invention is to provide a film having high break elongation property and capable of containing an antibacterial metal in a stabilized manner.

It is also an object of the present invention to provide a process for preparing polysaccharides.

It is an additional object of the present invention to provide a novel microorganism belonging to the genus Kliebsiella.

To a accomplish the aim, in a first aspect of the present invention, there is provided a humectant comprising a polysaccharide as an active principle, composed of D-glucuronic acid, L-rhamnose, D-galactose and D-glucose in a molar ratio of D-glucuronic acid:L-rhamnose:D-galactose:D-glucose=0.8–1.2:2.4–3.6:0.8–1.2:0.8–1.2.

In a second aspect of the present invention, there is provided a antistatic agent comprising a polysaccharide as an active principle, composed of D-glucuronic acid, L-rhamnose, D-galactose and D-glucose in a molar ratio of D-glucuronic acid:L-rhamnose:D-galactose:D-glucose= 0.8–1.2:2.4–3.6:0.8–1.2:0.8–1.2.

In a third aspect of the present invention, there is provided a film-forming agent comprising a polysaccharide as an active principle, composed of D-glucuronic acid, L-rhamnose, D-galactose and D-glucose in a molar ratio of D-glucuronic acid:L-rhamnose:D-galactose:D-glucose= 0.8–1.2:2.4–3.6:0.8–1.2:0.8–1.2.

In a fourth aspect of the present invention, there is provided a dispersant comprising a polysaccharide as an active principle, composed of D-glucuronic acid, L-rhamnose, D-galactose and D-glucose in a molar ratio of D-glucuronic acid:L-rhamnose:D-galactose:D-glucose= 0.8–1.2:2.4–3.6:0.8–1.2:0.8–1.2.

In a fifth aspect of the present invention, there is provided a process for preparing polysaccharides defined in the first to forth aspect comprises culturing the polysaccharide-productive *Kliebsiella oxytoca* TNM-3 strain (FERM BP-4669) or mutants thereof, and collecting from the culture a polysaccharide having a structure of the following formula as repeating unit:

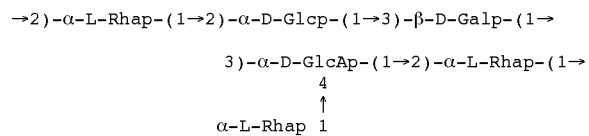

In a sixth aspect of the present invention, there is provided polysaccharide-productive *Kliebsiella oxytoca* TNM-3 strain (FERM BP-4669) and mutants thereof.

BRIEF DESCRIPTION OF THE DRAWING

FIG. 1 is an IR absorption spectrum of a polysaccharide obtained according to the process of the present invention.

DETAILED DESCRIPTION OF THE INVENTION

The present invention is described in detail below.

The polysaccharide produced and used in the present invention, as apparent from its constituent sugars shown above, is an acidic heteropolysaccharide. This polysaccharide usually has the following properties.
1) Form: White fiber-like (freeze-dried product).
2) Solubility: Soluble in water, dilute acids and dilute alkalis and insoluble in methanol, ethanol and acetone.
3) IR absorption spectrum: Absorptions are observed at around 3400 $cm^{-1}$, around 1620 $cm^{-1}$, 1100 $cm^{-1}$, 1250 $cm^{-1}$ and around 2950 $cm^{-1}$.
4) Color reactions: Positive in any of the phenolsulfuric acid test, carbazole-sulfuric acid test and m-phenylphenol test.

The polysaccharide produced and used in the present invention has following properties (a)–(c) preferably.
(a) Molecular Weight The molecular weight of the polysaccharide measured by gel permeation chromatography is approximately $1\times10^3$ to $1\times10^7$, preferably approximately $5\times10^3$ to $1\times10^7$.
(b) Bonding Pattern The bonding pattern and the molar ratio of the constituent sugar residues, viz. D-glucuronic acid, L-rhamnose, D-galactose and D-glucose are as shown below:

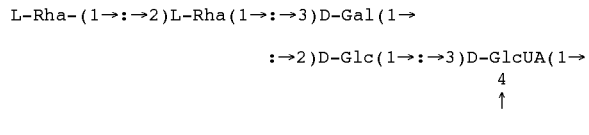

preferably 0.9–1.1:1.7–2.3:0.9–1.1:0.9–1.1:0.9–1.1.
(c) Bonding Position

D-glucuronic acid, L-rhamnose, D-galactose and D-glucose are bonded at α-position, at α-position, at β-position and at α-position, respectively.

The molecular weight of the polysaccharide and the kind, ratio and bonding pattern of the composing sugars of the polysaccharide used in the present invention can be determined by the conventional methods such as chromatographic analysis after hydrolysis, methylation analysis, Smith's degradation method, etc. For instance, the following methods may be employed for determination of the said items.

Determination of Molecular Weight

The molecular weight can be determined by GPC-mode high-performance liquid chromatography with an Asahipak GFA-7MF column (Asahi Chemical Co., Ltd.) and the mobile phase comprising a 0.1 M aqueous solution of sodium nitrate, using the standard calibration curve of molecular weight-retention time prepared by using pullulan of a known molecular weight as standard sample.

Constituent Sugars and Their Ratio

The polysaccharide and the one in which the carboxyl group of the uronic acid residue has been reduced (hereinafter referred to as carboxyl-reduced polysaccharide or simply reduced version) were hydrolyzed using 2M trifluoroacetic acid (TFA) at 100° C. for 6 hours and then converted into alditol acetates. The obtained derivatives were subjected to gas chromatographic analysis using a 3% ECNSS-M coated Gaschrom Q column (Wako Pure Chemicals Co., Ltd.). The constituent sugars of the polysaccharide and their ratio were determined from the analytical results obtained from the polysaccharide and its reduced version.

The polysaccharide used in the present invention can be obtained by culturing the polysaccharide-productive *Kliebsiella oxytoca* TNM-3 strain (FERM BP-4669) or mutants thereof and collecting the polysaccharide from the culture. The process is explained in detail below.

First, the polysaccharide obtained from the culture of *Kliebsiella oxytoca* TNM-3 strain (FERM BP-4669) or mutants thereof is explained.

The molecular weight of the polysaccharide determined by gel permeation chromatography is usually approximately $1 \times 10^3$ to $1 \times 10^7$, preferably $5 \times 10^3$ to $1 \times 10^7$. This molecular weight can be freely adjusted within the above-defined range by controlling the cultivation conditions or treatments after cultivation.

The polysaccharide obtained according to the process of the present invention has the following properties.

(1) Form
 White fibrous (freeze-dried product).

(2) Solubility
 Soluble in water, dilute acids and dilute alkalis and insoluble in methanol, ethanol and acetone.

(3) IR absorption spectrum
 The IR spectrum of the polysaccharide by the KBr tablet method is shown in FIG. 1. As is seen from FIG. 1, there are observed absorptions due to hydroxyl group at around 3400 $cm^{-1}$, carboxyl group of uronic acid at around 1620 $cm^{-1}$, ether bond at around 1100 $cm^{-1}$ and 1250 $cm^{-1}$, and alkane group at around 2950 $cm^{-1}$.

(4) Color reaction
 The results of the phenolsulfuric acid test and carbazole-sulfuric acid test of the polysaccharide in the present invention were positive, from which it was confirmed that this polysaccharide is an acidic polysaccharide containing uronic acid. The result of the m-phenylphenol test of the polysaccharide was also positive.

(5) Analysis of composing sugars
 The polysaccharide produced according to the process of the present invention and its carboxyl-reduced version were subjected to acid hydrolysis with 2M trifluoroacetic acid (TFA) at 100° C. for 6 hours and derived into alditol acetates. The gas chromatograph analysis of the resulting derivatives were carried out by using a 3% ECNSS-M coated Gaschrom Q column (Wako Pure Chemicals Co., Ltd.). There were detected the peaks with the same retention times as those of the derivatives obtained from L-rhamnose, D-glucose and D-galactose.

From the calibration curves determined up by using the derivatives obtained from L-rhamnose (L-Rha), D-glucose (D-Glc) and D-galactose (D-Gal), the compositional ratios (molar ratios) of the composing sugars of said two kinds of polysaccharide were calculated as the closest integral ratios. The results are shown in Table 1.

TABLE 1

|  | L-Rha | D-Glc | D-Gal |
|---|---|---|---|
| Polysaccharide in which carboxyl group of uronic acid residue is not reduced | 2 | 1 | 1 |
| Polysaccharide in which carboxyl group of uronic acid residue has been reduced | 3 | 2 | 1 |

In view of the fact that the molar ratios of L-rhamnose and D-glucose to D-galactose in the carboxyl-reduced polysaccharide are higher than that in the non-reduced polysaccharide as shown in Table 1, and since there exists no corresponding uronic acid in rhamnose, the uronic acid contained as a constituent sugar in the polysaccharide obtained from the process of the present invention was identified as D-gluconic acid. Also, from the increase of the molar ratio of L-rhamnose, it was determined that part of the L-rhamnose residue existed as aldobiouronic acid unit having relatively high resistance to hydrolysis. These facts confirmed that the polysaccharide obtained from the process of the present invention was composed of L-rhamnose (L-Rha), D-glucose (D-Glc), D-galactose (D-Gal) and D-glucuronic acid (D-GlcUA) in a molar ratio of L-Rha:D-Glc:D-Gal:D-GlcUA=3:1:1:1, and that the said polysaccharide has a D-GlcUA-L-Rha unit as part of its molecular structure.

After the acid hydrolysis, the polysaccharide produced according to the process of the present invention was subjected to the same gas chromatographic analysis as described above except for use of 0.2M TFA. The molar ratios of D-glucose and D-galactose to L-rhamnose were lower than that of the analysis which used 2M TFA. These facts suggest that the said polysaccharide is relatively susceptible to acid hydrolysis and has a structural segment where the L-rhamnose residues are arranged successively or an L-rhamnose residue is positioned at the terminal.

(6-1) Bonding pattern of constituent sugar residues (by methylation analysis)

The polysaccharide obtained according to the process of the present invention and its reduced version in which carboxyl group of uronic acid residue has been reduced were first methylated by the Hakomori method, then subjected to acid hydrolysis with 88% formic acid at 100° C. for 16 hours, followed by evaporation to remove formic acid and additional acid hydrolysis with 2M TFA at 100° C. for 6 hours, and the resultant derivatives were converted into alditol acetates. The gas chromatograph analyses of them were carried out with a 3% ECNSS-M coated Gaschrom Q column (Wako Pure Chemicals Co., ltd.).

As a result, from the analysis of the polysaccharide in which carboxyl group of uronic acid residue was not reduced, there were detected peaks with the same retention times as those of the derivatives obtained from 2,3,4-tri-O-methyl-L-rhamnose, 3,4-di-O-methyl-L-rhamnose, 3,4,6-tri-O-methyl-D-glucose and 2,4,6-tri-O-methyl-D-galactose, and from the analysis of the polysaccharide in which carboxyl group of uronic acid residue has been reduced, there were detected peaks with the same retention times as those of the derivatives obtained from 2,3,4-tri-O- methyl-L-rhamnose, 3,4-di-O-methyl-L-rhamnose, 3,4,6-tri-O-methyl-D-glucose, 2,6-di-O-methyl-D-glucose and 2,4,6-tri-O-methyl-D-galactose.

From these results, it was confirmed that the bonding pattern of the constituent sugar residues in the polysaccharide obtained from the process of the present invention was as follows: L-rhamnose residue: Rha(1→ and →2)Rha(1→; D-glucose residue: →2)Glc(1→; D-galactose residue: 3)Gal (1→; and D-glucuronic acid residue: as shown below:

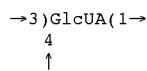

Also, from the calibration curve determined by using the derivatives obtained from 2,3,4-tri-O-methyl-L-rhamnose, 3,4-di-O-methyl-L-rhamnose, 3,4,6-tri-O-methyl-D-glucose, 2,6-di-O-methyl-D-glucose and 2,4,6-tri-O-methyl-D-galactose, it was determined that the molar ratio of the constituent sugar residues of the polysaccharide obtained from the process of the present invention is as shown below, when the molar ratio is expressed by the difference of the bonding pattern and represented by the closest integral ratio.

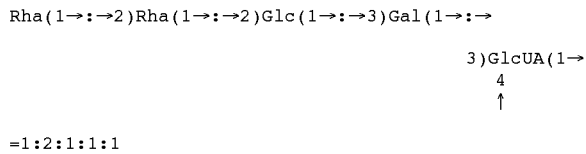

Further, when the derivatives obtained from the acid hydrolysis of the polysaccharide of the present invention were subjected to gas chromatography-mass spectral (GC-MS) analysis using a DB1 column (J & W Scientific Inc.), there were observed the cleavage patterns agreeing with those obtained in similar analysis of 1,5-di-O-acetyl-6-deoxy-2,3,4-tri-O-methylhexitol, 1,2,5-tri-O-acetyl-6-deoxy-3,4-di-O-methylhexitol, 1,2,5-tri-O-acetyl-3,4,6-tri-O-methylhexitol and 1,3,5-tri-O-acetyl-2,4,6-tri-O-methylhexitol. In case of using the polysaccharide in which carboxyl group of uronic acid residue has been reduced, the GC-MS analysis gave the same cleavage patterns as obtained in similar analysis of 1,5-di-O-acetyl-6-deoxy-2,3,4-tri-O-methylhexitol,1,2,5-tri-O-acetyl-6-deoxy-3,4-di-O-methylhexitol, 1,2,5-tri-O-acetyl-3,4,6-tri-O-methylhexitol, 1,3,5-tri-O-acetyl- 2,4,6-tri-O-methylhexitol and 1,3,4,5-tetra-O-acetyl-2,6-di-O-methylhexitol. The results of these GC-MS analyses gave a support to the above-described analytical results.

(6-2) Analysis of bonding pattern of constituent sugar residues (complete Smith degradation)

The polysaccharide obtained from the process of the present invention and its reduced version were subjected to periodate oxidation at room temperature for 8 days using 0.03M sodium periodate, followed by 6-hour acid hydrolysis at 100° C. with 2M TFA, and the hydrolysates were converted into acetates after reduced with sodium boron hydride.

As a result of gas chromatographic analysis of the same manner as in the methylation analysis described in (6-1) above, in the case of the non-carboxyl-reduced polysaccharide, there were detected peaks with same retention times as those of the derivatives obtained from D-glycerol and D-galactose and an unidentified peak which is suggested attributable to the complete Smith degradation product of the L-rhamnose residue, and in the case of the carboxyl-reduced polysaccharide, there were detected peaks with same retention times as those of the derivatives obtained from D-glycerol, D-glucose and D-galactose and an unidentified peak which is suggested attributable to the complete Smith degradation product of the L-rhamnose residue.

In both cases of the polysaccharide obtained from the process of the present invention and its reduced version, since no L-rhamnose was detected, the bonding pattern of the L-rhamnose residue can be determined to be Rha(1→, →2)Rha(1→ or →4)Rha(1→ which is subject to periodate oxidation, and the bonding pattern of the D-galactose residue detected in both above cases can be determined to be →3)Gal(1→ or a graft such as shown below which is not subject to periodate oxidation:

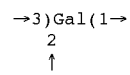

Regarding the bonding pattern of the D-glucose residue, in the case of the polysaccharide in which carboxyl group of uronic acid residue has been reduced, since D-glycerol was detected in the analysis, it can be determined that said bonding pattern should be Glc(1→, →2)Glc(1→ or →6)Glc (1→ which is subject to periodate oxidation, and regarding the bonding pattern of the D-glucuronic acid residue, since D-glucose which was not detected in the polysaccharide in which carboxyl group of uronic acid residue has been reduced was detected in the carboxyl-reduced polysaccharide, said bonding pattern can be determined to be →3)GlcUA(1→ or a graft such as shown below which is not subject to periodate oxidation:

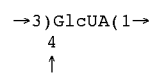

These results support the above-described methylation analysis results.

(7) Optical rotation $[\alpha]^{25}_D=+55°$ (c=0.5, aqueous solution).

From the optical rotation and the results of the analyses of the composing sugars, the anomers of the composing sugar residues of the polysaccharide obtained from the process of the present invention are considered as follows: α for L-rhamnose, α for D-glucose, β for D-galactose and α for D-glucuronic acid.

The above analytical results agree with the analytical data on the capsular polysaccharides of Klebsiella K19 strain illustrated in Carbohydrate Research, Vol. 157, pp. 13–25, 1986. Also, the results of $^1$H- and $^{13}$C-NMR spectral measurements show that the chemical shift of each peak detected on the spectra of the polysaccharide obtained from the process of the present invention agrees with the data shown in the above literature. These facts indicate that the polysaccharide obtained from the process of the present invention is of a structure whose main repeating unit is represented by the following formula. It has been unknown that a microorganism other than Klebsiella K19 strain could produce a polysaccharide having this repeating unit.

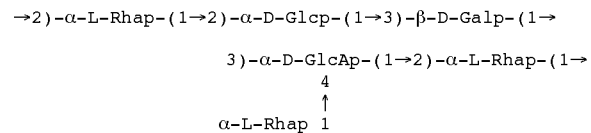

In the process of the present invention, polysaccharide-productive *Klebsiella oxytoca* TNM-3 strain (FERM BP-4669) or a mutant thereof is used as microorganism. The mutant of said strain can be generated by a known mutagenetic means such as application of ultraviolet ray or radiation such as X-ray or use of a chemical mutagen such as ethylmethanesulfonic acid (EMS) or N-methyl-N'-nitro-N-nitrosoguanidine (MNNG). The ability of a microorganism to produce said polysaccharide can be easily known by analyzing the culture of its strain.

The bacteriological properties of Klebsiella oxytoca TNM-3 strain are shown in Tables 2–4.

TABLE 2

Bacteriological properties:

| Form: | Bacillus. Colony is rather mucoidal. |
|---|---|
| Gram-stain: | − |
| Glucose OF: | F type |
| Motility: | − |
| Catalase: | + |
| Oxidase: | − |
| Gas generation from glucose: | + |
| Growth with KCN medium: | + |
| Citrate utilization: | + |
| Methyl red: | − |
| VP | + |

TABLE 3

Acid generation from carbohydrates:

| Glucose | + |
|---|---|
| Adonitol | + |
| Arabinose | + |
| Dulcitol | + |
| Lactose | + |
| Maltose | + |
| Mannitol | + |
| Rhamnose | + |
| Salicin | + |
| Sorbitol | + |
| Sucrose | + |
| Trehalose | + |
| Xylose | + |
| Glycerol | + |
| Inocitol | + |
| Raffinose | + |

TABLE 4

| Gelatin hydrolysis | − |
|---|---|
| Malonate | + |
| Gluconate | + |
| Nitrate reduction | + |
| Gas generation from nitrate | − |
| Urease | + |
| Lysine decarboxylase | + |
| Alginine dihydrase | − |
| Ornithine carboxylase | − |
| PAA | − |
| ONPG | + |
| Hydrogen sulfide | + |
| Aesculin hydrolysis | + |
| Indole | + |

Extracellular polysaccharide productivity+(Ability to produce polysaccharide having said specific recurring unit)

From the above bacteriological properties, the bacterial strain of the present invention was determined to belong to the genus Klebsiella as the bacteriological properties agree with the data on the culture type Klebsiella oxytoca described in Bergey's Manual of Systematic Bacteriology, Vol. 1, page 462, 1984, although there is no description for extracellular polysaccharide productivity in this literature. Since no strain having an extracellular polysaccharide productivity is known in the Klebsiella oxytoca species, the strain of the present invention is deemed as a new strain of Klebsiella oxytoca having an extracellular polysaccharide productivity. Thus this strain was named Klebsiella oxytoca TNM-3 strain. Klebsiella K-19 strain described in the Carbohydrate Research mentioned above belongs to the Klebsiella pneumonia species.

The strain of the present invention has been deposited at the Life Science and Engineering Research Institute, the Agency of Industrial Science and Technology, the Ministry of International Trade and Industry as international deposition under "FERM BP-4669" since May 18, 1994.

The medium used for culturing the said microorganism in the process of the present invention is not specified; it is possible to use any medium, as far as it allows growth of the microorganisms belonging to the genus Klebsiella, such as suitable amounts of carbon source, nitrogen source, inorganic salt and micronutrients to produce polysaccharide. As carbon source, glucose, lactose, maltose, xylose, mannitol, scrose, rhamnose, arabinose, trehalose, raffinose and the like can be used. As nitrogen source, synthetic compounds such as nitrates, ammonium salts, urea, etc., and natural organic substances such as polypeptone, corn steep liquor, yeast extract, meat extract, defatted soybean extract, peptide, amino-acids, etc., can be used. As inorganic salt, phosphates, potassium salts, sulfates, magnesium salts and the like can be used. In the medium may be added iron salts, calcium salts, manganese salts and the like, if necessary. Yeast extract, various vitamins and such may be used as micronutrients.

The state of the culture medium used in the process of the present invention may be either solid or liquid. In case of using a liquid medium, shaking culture or aerated spinner culture is preferred to static culture because of higher yield of polysaccharide. The cultivation pH is not restricted as far as it allows growth of the present microorganism and extracellular polysaccharide productivity, but usually it is in the range 4–8. Cultivation temperature is also not specified, but it is usually between 20° C. and 35° C. Cultivation time is selected so that the polysaccharide yield will be maximized, but usually a period from one to 7 days is appropriate.

Conventional methods can be employed for collecting the objective polysaccharide from the culture. For instance, first the bacterial cells are removed from the culture by a suitable means such as centrifugation or filtration, then an organic solvent such as methanol, ethanol, isopropanol or acetone is added to the culture to cause precipitation, the precipitate is dissolved in water and dialyzed against water, and the dialyzate is dried by an appropriate method such as draft drying, hot-air drying, spray drying, drum drying, vacuum drying, freeze-drying, etc., to recover the polysaccharide.

It is also possible to employ a method in which the substances other than the objective polysaccharide are removed from the culture by ultrafiltration, and the concentrated solution is subjected to the above drying operation. If necessary, the produced polysaccharide may be purified by a conventional method to obtain a high-purity polysaccharide. For the purification, there may be employed various types of column chromatography such as ion-exchange, gel filtration or various column chromatographies such as affinity chromatography, sedimentation or salting-out by use of a quaternary ammonium salt, and sedimentation by use of an organic solvent.

The degree of polymerization of the polysaccharide obtained from the process of the present invention can be varied by controlling the cultivation conditions such as medium composition, collection method, etc. Also, the collected or purified product may be hydrolyzed using TFA, formic acid, hydrochloric acid or the like and controlling the operating conditions. Therefore, it is possible to freely adjust the molecular weight of the produced polysaccharide within the range from about $1 \times 10^3$ to about $10 \times 10^6$.

The polysaccharide obtained in the manner described above has many useful properties such as moisture retainability, film-forming properties and dispersibility. Regarding moisture retention, the said polysaccharide has the nature that the moisture retainability of the said polysaccharide is less affected by the ambient humidity than that of sodium hyaluronate which is a representative known humectants. From the aspect of moisture retention, the polysaccharide with a molecular weight of about $10^5$–$10^6$ is preferably used.

The polysaccharide used in the present invention can also be obtained by culturing Klebsiella K-19 strain described in Carbohydrate Research, Vol. 157, pp. 13–25 (1986) and collecting the objective polysaccharide from the culture in the manner described above.

The polysaccharide used in the present invention has an excellent moisture retainability and also shows a tyrosinase-inhibitory activity.

The cosmetic compositions provided according to the present invention are now explained. The cosmetic compositions of the present invention can be obtained by blending said polysaccharide as humectant in the base material. The polysaccharide is blended in an amount of usually 0.0001 to 20% by weight, preferably 0.001 to 10% by weight based on the whole composition. When the amount of the polysaccharide blended is less than 0.0001% by weight, the effect of the polysaccharide may be insufficient. Also, when the amount of polysaccharide is blended in excess of 20% by weight, the obtained cosmetic compositions may be bad in feeling of use.

The cosmetic composition of the present invention can be used in various forms of preparation such as water-in-oil type or oil-in-water type emulsion, cream, milky lotion, beauty wash, oleaginous cosmetics, rouge, foundation, hair tonic, hair dressing, hair tonic, hair grower, and other hair and skin cosmetics.

In the preparation of the cosmetic composition of the present invention, there can be used as oleaginous component hydrocarbons such as liquid paraffin, paraffin wax, ceresine, squalane, etc., waxes such as beeswax, spermaceti, carnauba wax, etc., natural animal and vegetable oils such as olive oil, camellia oil, jojoba oil, lanoline, etc., silicone oil, fatty acids, higher alcohols, and their ester oils. These oleaginous substances are preferably used in an amount of 0 to 50% by weight.

The surfactants usable in the present invention include, as preferred examples, polyoxyethylene alkyl ethers, polyoxyethylene fatty acid esters, polyoxyethylene sorbitan fatty acid esters, polyoxyethylene sorbitol fatty acid esters, polyoxyethylene hardened castor oil alkylsulfates, polyoxyethylene alkylsulfates, alkyl phosphates, polyoxyethylene alkylphosphates, fatty acid alkali metal salts, sorbitan fatty acid esters, and glycerol fatty acid esters. The surfactant is preferably used in an amount of 0 to 10% by weight.

The following substances may be properly added as optional components according to the type and the purpose of use of the cosmetic preparation produced.

Viscosity modifier: high-molecular weight compounds such as polyvinyl alcohol, carboxyvinyl polymer, carboxymethyl cellulose, polyvinyl pyrrolidone, hydroxyethyl cellulose and methyl cellulose, natural gums such as gelatin and traga- canth gum, and alcohols such as ethanol and isopropanol. The preferable amount used thereof is 0 to 30% by weight.

Humectant: propylene glycol, glycerol, 1,3-butylene glycol, dipropylene glycol, sorbitol, lactic acid, sodium lactate, sodium pyrrolidonecarboxylate, etc. The preferable amount used thereof is 0 to 50% by weight.

Antiseptic: paraoxybenzoic acid ester, benzoic acid, sodium benzoate, sorbic acid, potassium sorbate, phenoxyethanol, etc. The preferable amount used thereof is 0.01 to 1% by weight.

Since the polysaccharide used in the present invention has excellent antistatic properties, the antistatic agent of the present invention containing the said polysaccharide is useful for antistatic agents for synthetic fiber and plastic products and it can be also applied to paints such as antistatic paint, electroconductive paint, etc. Further, since the polysaccharide used in the present invention has high safety characteristics such as low toxicity and low stimulation, the antistatic agent of the present invention can be particularly used in the field of articles where safety is required, such as clothing and articles for hair treatment.

The antistatic agent of the present invention is used in practical by either coating on or incorporating in the base material. Coating can be accomplished by a conventional method, such as dissolving or mixing the antistatic agent in a commonly used diluent and spraying the solution to the base material such as fibers or fabrics, or immersing the base material in a solution or mixed solution of the antistatic agent. Incorporation can also be accomplished by known methods.

The amount of the antistatic agent to be applied is properly selected in conformity to the base material, application way and other factors, but usually it is applied in an amount of 0.2 to 20 g/m$^2$ of surface area of the base material in the case of coating and 0.3 to 30% by weight based on the base material in the case of incorporation.

Since the polysaccharide used in the present invention has an excellent dispersibility for the inorganic or oleaginous substances, it is expected that the dispersant of the present invention containing the said polysaccharide can be used in various fields of products such as paints, medical and dental supplies, contrast medium, structural and ceramic materials, cosmetics, foods, medicines, etc.

The amount of the dispersant used is properly selected according to the type of the dispersoid, etc., but it is usually in the range of 0.01–10 w/v % based on the dispersing medium.

The polysaccharide used in the present invention can form an aqueous solution having a substantially same degree of viscosity as provided by pullulan which is popularly used as film-forming material, so that a high-concentration solution can be easily prepared from the said polysacoharide and a film can be produced efficiently therefrom. Also, since this polysaccharide has glucuronic acid residues, it is possible to afford antibacterial properties to the film by substituting the counter ions of the said acid residues with an antibacterial metal such as silver, copper or zinc. It is also remarkable that the film made by using this film-forming agent has high break elongation property. Thus, the polysaccharide used in the present invention has the useful properties as film-forming agent not possessed by the conventional polysaccharides.

The film-forming agent of the present invention can be made into a film by forming an aqueous solution of the agent, casting the solution or coating or spraying it to the base material, and drying the cast solution or coating. The operating conditions such as concentration of the solution and drying temperature may be properly selected, but usually the solution concentration is 1 to 35 w/v % and the drying temperature is 20 to 150° C.

The film of the present invention obtained in the manner described above has a break elongation of usually not less than 5%, preferably not less than 6%, and a tensile strength of usually not less than 400 kg/cm².

The humectant provided according to the present invention has higher stability and better moisture retainability than the conventional humectants and also has a tyrosinase-inhibitory activity. Because of these properties, this humectant can be a useful component of cosmetics. The humectant of the present invention also can be used as a treating agent in production of moisture-permeable clothing, an adjunct for improving moisture retainability of foods, a moisture-controlling auxiliary structural material and the like. Also, the polysaccharide used in the present invention can be utilized for other purposes than cosmetic application, such as for preventing browning of meat or blacking of cultured fishes because of its tyrosinase-inhibitory activity.

The antistatic agent provided according to the present invention has higher degree of more excellent biodegradability and higher safety than the synthetic polymer-type antistatic agents. Since the polysaccharide used in the present invention not only has high antistatic performance but also low toxicity and stimulation, the antistatic agent of the present invention comprising the said polysaccharide can be used favorably in the field where safety is an important factor, such as clothing and hair treatments.

The dispersant of the present invention have an excellent dispersibility for the inorganic or oleaginous substances.

The film-forming agent of the present invention can provide an aqueous solution having low viscosity and make a film with high break elongation property. It can also contain an antibacterial metal as counter ions. The film-forming agent of the present invention can be utilized as a packaging film material for foods, cosmetics, medicines, agricultural products, dyes, etc., and a coating material for the tablets and grains of detergents, agricultural chemicals, germicides, dye-assist agents, etc. Utilization of said film-forming agent as material of the electrolyte portion of film battery is also expected. The films made by using the film-forming agent of the present invention are outstanding for their high break elongation property.

According to the process of the present invention, it is possible to produce a specific polysaccharide at high efficiency.

EXAMPLES

The present invention is explained in more detail in the following Examples, but it should be recognized that the scope of the present invention is not restricted to these Examples.

Example 1

A 100 ml of a culture medium of the composition shown in Table 5 was put into each of the four 500-ml Sakaguchi's flasks and subjected to 20-minute moist heat sterilization at 121° C. Then one platinum loopful of *Klebsiella oxytoca* TNM-3 strain (FERM BP-4669), which has been liquid-shaking cultured in a test tube for 2 days using a medium of the composition shown in Table 5 was inoculated in said medium in each flask and subjected to reciprocal shaking culture at a shaking frequency of 110 strokes per minute at 28° C. for one day.

TABLE 5

| Medium composition (wt %) | |
| --- | --- |
| Glucose | 1% |
| Polypeptone | 0.1% |
| Potassium dihydrogenphosphate | 0.15% |
| Magnesium sulfate heptahydrate | 0.05% |
| Vitamin $B_1$ | 0.0005% |
| Biotin | 0.000006% |
| Calcium pantothenate | 0.001% |
| Nicotinamide | 0.0005% |
| pH | 6.5 |

The 400 ml of the resultant culture was inoculated in 8 liters of a medium of the composition shown in Table 6 which had been sterilized therein in the same manner as described above and kept in a 15-liter jar fermentor, and subjected to 86-hour aerated spinner culture under the conditions of 28° C. and aeration of 8 liter/min with pH maintained at 7 by using a 5M sodium hydroxide solution. The spinner speed was controlled to be 200 r.p.m. through the period of first 14 hours from start of culture, 300 r.p.m. in the next 7-hour period, 550 r.p.m. during the succeeding period of 41 hours, and 650 r.p.m. in the last 24-hour period.

TABLE 6

| Medium composition (wt %) | |
| --- | --- |
| Glucose | 4% |
| Polypeptone | 0.2% |
| Potassium dihydrogenphosphate | 0.15% |
| Magnesium sulfate heptahydrate | 0.01% |
| Vitamin $B_1$ | 0.00009% |
| Vitamin $B_2$ | 0.000046% |
| Vitamin $B_6$ | 0.000022% |
| Vitamin $B_{12}$ | 0.00000016% |
| Biotin | 0.0000009% |
| Calcium pantothenate | 0.000120% |
| Nicotinamide | 0.000336% |
| Folic acid | 0.00000114% |

The resulting culture was diluted 5-fold with water and subjected to 20-minute moist heat sterilization at 121° C., after which the bacterial cells were removed by centrifugation. The supernatant was subjected to cross-flow ultrafiltration repeatedly until the substances other than the polysaccharide of the present invention such as residual medium components have been removed. Ultrafiltration was carried out by using an ultrafiltration system "UF-LMSII" (fractional molecular weight: $3 \times 10^6$) mfd. by Toso Co., Ltd. The concentrated solution which unpassed through the ultrafilter was freeze-dried to give 15.0 g of a single polysaccharide per liter of the medium. The singleness of polysaccharide was confirmed by using GPC-mode high-performance liquid chromatography.

The molecular weight of the obtained polysaccharide was determined by high-performance liquid chromatography using an Asahipak GFA-7MF column (Asahi Chemical Industry Co., Ltd.) with a 0.1M $NaNO_3$ solution as mobile phase. As a result, the retention time at the peak top on the chromatograph of the polysaccharide showed a value corresponding to the molecular weight of about $2.7 \times 10^6$ on the molecular weight-retention time calibration determined by using pullulan of the known molecular weight as standard sample.

The above polysaccharide and its reduced version in which the carboxyl group of glucuronic acid residue has been reduced were hydrolyzed down to the composing sugars, then derived to alditol acetates and the gas chromatograph analyses thereof were carried out. The molar ratio of the constituent sugars was determined from the previously prepared calibration curves and the peak areas of the respective constituent sugars and the following result was obtained: D-glucuronic acid:L-rhamnose:D-galactose:D-glucose=1:3:1:1.

Example 2

A 100 ml of a medium of the composition shown in Table 7 was subjected to 20-minute moist heat sterilization at 121° C. in a 500-ml Sakaguchils flask, and then one platinum loopful of *Klebsiella oxytoca* TNM-3 strain, which has liquid-shaking cultured in a test tube for 2 days using a medium of the composition shown in Table 5, was inoculated into said medium in the flask and subjected to reciprocal shaking culture at a shaking frequency of 110 strokes per minute at 28° C. for one day.

TABLE 7

| Medium composition (wt %) | |
| --- | --- |
| Glucose | 2.0% |
| Polypeptone | 0.1% |
| Dipotassium hydrogenphosphate | 0.15% |
| Magnesium sulfate heptahydrate | 0.05% |
| Vitamin $B_1$ | 0.0005% |
| Biotin | 0.000006% |
| Calcium pantothenate | 0.001% |
| Nicotinamide | 0.0005% |
| pH | 6.5 |

The 400 ml of the resultant culture was inoculated in 8 liters of a medium of the composition shown in Table 8, which had been sterilized therein in the same manner as described above and kept in a 15-liter jar fermentor, and subjected to 95-hour aerated spinner culture under the conditions of 28° C. and aeration of 5 l/min with pH maintained at 7 by using a 5M sodium hydroxide solution. The spinner speed was controlled to be 200 r.p.m. through the period of the first 24 hours from start of culture, 400 r.p.m. in the next 9-hour period, and 700 r.p.m. in the last 62-hour period.

TABLE 8

| Medium composition (wt %) | |
| --- | --- |
| Glucose | 4% |
| Polypeptone | 0.2% |
| Dipotassium hydrogenphosphate | 0.15% |
| Magnesium sulfate heptahydrate | 0.01% |
| Vitamin $B_1$ | 0.0005% |
| Biotin | 0.000006% |
| Calcium pantothenate | 0.001% |
| Nicotinamide | 0.0005% |

The resulting culture was adjusted to a pH of 4.5 with 10% sulfuric acid and subjected to moist heat sterilization at 121° C. for 20 minutes, after which the bacterial cells were removed by centrifugation. Thereafter, the same treatments as in Example 1 were carried out to obtain 21.0 g of a single polysaccharide per liter of the medium. The molecular weight of the obtained polysaccharide determined in the same way as in Example 1 was approximately $1.5 \times 10^6$.

The above polysaccharide and its reduced version in which carboxyl group of glucuronic acid residue has been reduced were hydrolyzed down to constituent sugars, then derived to alditol acetates and the gas chromatograph analyses thereof were carried out. The molar ratio of the constituent sugars was determined from the previously prepared calibration curves and the peak areas of the respective constituent sugars, and the following result was obtained: D-glucuronic acid:L-rhamnose:D-galactose:D-glucose=1:3:1:1.

Example 3

A culture obtained by the method as in Example 2 was adjusted to a pH of 4.5 with 10% sulfuric acid and subjected to moist heat sterilization at 121° C. for 100 minutes, after which the bacterial cells were removed by centrifugation. Thereafter, the same treatment as in Example 2 except for the ultrafiltration treatment carried out by using an ultrafiltration system "UF-LMSII" (fractional molecular weight: $1 \times 10^6$) mfd. by Toso Co., Ltd., 19.0 g of a single polysaccharide per liter of the medium was obtained. The molar ratio of the constituent sugars was determined in the same way as in Example 1 and the following result was obtained: D-glucuronic acid:L-rhamnose:D-galactose:D-glucose=1:2.8:1:1. The molecular weight of obtained polysaccharide determined in the same way as in Example 1 was approximately $2 \times 10^5$.

Example 4

The polysaccharide obtained in Example 1 was dissolved in purified water to prepare a 1% (w/v) aqueous solution, and this solution was put into a 60-ml small-sized pressure vessel and treated therein under 10 atm at 180° C. for 10 minutes. The molecular weight of the polysaccharide after the treatment, determined in the same way as in Example 1, was approximately $1.2 \times 10^4$.

The above polysaccharide and its reduced version in which carboxyl group of glucuronic acid residue were hydrolyzed down to the constituent sugars, the derived to alditol acetates and the gas chromatograph analyses thereof were carried out. The molar ratio of the constituent sugars was determined from the previously prepared calibration curves and the peak areas of the respective constituent sugars and the as following result was obtained: D-glucuronic acid:L-rhamnose:D-galactose:D-glucose=1:3:1:1.

Test Example 1 (Safety test)

Using the polysaccharide obtained in Example 1, the safety to toxicity and irritating effect on the skin were evaluated and the results are shown in Table 9. A 50% (w/v) suspension was used for the skin irritation test. The evaluation criterion for skin irritating effect is shown in Table 10.

TABLE 9

| | |
| --- | --- |
| Acute oral toxicity (LD50, in rats): (LD50, in rats) | >5000 mg/kg (practically harmless) |
| Primary skin irritating: effect (Draize's method) | primary irritation index 0.2 (weak irritant) |

TABLE 10

| Evaluation of skin irritating effect | Primary irritation index (PII) |
| --- | --- |
| Non-irritant | 0 |
| Weak irritant | $0 < PII \leq 2$ |
| Medium irritant | $2 < PII \leq 5$ |
| Strong irritant | $5 <$ |

The above results show that the polysaccharide used in the present invention is low in acute oral toxicity and practically harmless, and its irritating effect on the skin is also of a level close to zero, which attests to high safety quality of this polysaccharide.

By way of comparison, the similar primary skin irritation test was carried out on a 4% (w/v) aqueous solution of sodium lauryl sulfate (produced by Wako Pure Chemicals Co., Ltd.) which is an antistatic agent generally used as a material of flatware washing detergents. The primary irritation index of this substance was 4.0 (medium irritant).

Example 5 (Moisture retainability in low-humidity environment)

The polysaccharides obtained in Examples 2 and 3 were put into the respective weighing tubes, perfectly vacuum-dried, then put into a desiccator adjusted to a relative humidity of 20% with potassium acetate, and left therein for 3 days. The above operations were carried out at a constant temperature of 20° C.

For the sake of comparison of moisture retainability, the similar operations were carried out on the commercially available humectants sodium hyaluronate derived from cockscomb (molecular weight: approx. $2\times10^6$, available from Cupie Co.), sodium hyaluronate produced by microbial fermentation (molecular weight: approx. $2\times10^6$, available from Kibun Food Chemifa Co., Ltd.), chitosan (produced by Ajinomoto Co., Ltd.), glycerol (produced by Wako Pure Chemical Industry Co., Ltd.) and sodium pyrrolidonecarboxylate, and the commercially available polysaccharides xanthan gum (produced by Kelco Corp.), carrageenan (produced by Dai-Nippon Pharmaceutical Co., Ltd.) and pullulan (produced by Hayashibara Biochemical Research Center Co., Ltd.).

The sample weight was measured periodically and he moisture retention percentagewas calculated from the following equation. The results are shown in Table 11.

Moisture retention percentage(%)=(A−B)/B×100 (wherein A is sample weight when it became constant, and B is dry sample weight).

TABLE 11

| Material | Moisture retention |
|---|---|
| Polysaccharide obtained in Example 1 | 12.1% |
| Polysaccharide obtained in Example 3 | 12.7% |
| Sodium hyaluronate derived from cockscomb | 12.0% |
| Sodium hyaluronate produced by microbial fermentation | 12.5% |
| Chitosan | 10.3% |
| Glycerol | 6.9% |
| Sodium pyrrolidonecarboxylate | 8.5% |
| Xanthan gum | 10.4% |
| Carrageenan | 9.3% |
| Pullulan | 8.8% |

As is seen from the above results, the moisture retentions of the polysaccharides used in the present invention are equal to or higher than that of the hyaluronates known as representative examples of conventional humectants, and also are a higher level of moisture retention than the commercial polysaccharides generally used as humectant, i.e., chitosan, glycerol and sodium pyrrolidonecarboxylate, even under a low-humidity environment of 20% RH. These facts indicate that the humectant provided according to the present invention has favorable properties for use in low-humidity environments.

Example 6 (Moisture retention in high-humidity environment)

The polysaccharides obtained in Examples 2 and 3 were perfectly vacuum dried in the respective weighing tubes, then put into a desiccator adjusted to a relative humidity of 92.9% with ammonium dihydrogenphosphate and left therein for 3 days. The above operations were carried out at a constant temperature of 30° C.

The same operations were carried out on sodium hyaluronate, derived from cockscomb, sodium hyaluronate produced by microbial fermentation, glycerol and sodium pyrrolidonecarboxylate which were used in Example 5.

The results are shown in Table 12. Moisture retention percentage was calculated in the same way as in Example 5.

TABLE 12

| Moisture | Material retention percentage |
|---|---|
| Polysaccharide obtained in Example 2 | 67.6% |
| Polysaccharide obtained in Example 3 | 56.5% |
| Sodium hyaluronate derived from cockscomb | 94.2% |
| Sodium hyaluronate produced by microbial fermentation | 96.9% |
| Glycerol | 139.1% |
| Sodium pyrrolidonecarboxylate | 218.3% |

Because of the spread of air conditioning, the interior environment of the working office is kept low in temperature and humidity even in the summer season, so that the moisture-retaining type of cosmetics such as used in the winter season are required throughout the year. However, since the outdoor environment in the summer season is high in temperature and humidity, the user of a cosmetic preparation containing a highly hygroscopic humectant could experience a sense of stickiness to the skin when the user goes out of doors for going or returning to home from the office or on other occasions such as lunching.

However, as is seen from the above results, the moisture retention percentageor hygroscopicity of the polysaccharides used in the present invention in a high-humidity environment with RH of 92.9% is lower than that of the conventional humectants, and they will not give a sense of tackiness to the skin of the user of the cosmetics containing said polysaccharides nor they adsorb moisture from the skin. It will be noted that the humectant of the present invention shows excellent performance even when exposed to a high-humidity environment.

Example 7 (Influence of chance of relative humidity on moisture retainability)

The polysaccharides obtained in Examples 2 and 3 were perfectly vacuum dried in the respective weighing tubes, then put into a desiccator adjusted to a relative humidity of 79% with ammonium chloride and left therein for 3 days. Then the polysaccharides were transferred into another desiccator adjusted to a relative humidity of 31% with calcium chloride hexahydrate and left therein for 3 days. The above operations were carried out at a constant temperature of 25° C.

The same operations were carried out on sodium hyaluronate derived from cockscomb and sodium hyaluronate produced by microbial fermentation used in Example 5.

The results are shown in Table 13. Moisture retention percentage was calculated in the same way as in Example 5.

TABLE 13

| Material | Moisture retention percentage at different relative humidities | | |
|---|---|---|---|
| | 79% | 31% | difference |
| Polysaccharide obtained in Example 2 | 37% | 25% | 12% |
| Polysaccharide obtained in Example 3 | 35% | 25% | 10% |
| Sodium hyaluronate derived from cockscomb | 46% | 27% | 19% |
| Sodium hyaluronate produced by microbial fermentation | 41% | 26% | 15% |

As is seen from the above results, each material tested can meet the standard requirement for 10–50% moisture retention under an ordinary environment with 40–80% RH. However, the influence by the change of relative humidity varies among the materials, that is, the difference between moisture retention percentage when RH is 79% and moisture retention percentage when RH is 31%, is 19% in the case of sodium hyaluronate derived from cockscomb and 15% in the case of sodium hyaluronate produced by microbial fermentation whereas it is only 12% and 10% in the case of the polysaccharides obtained according to the present invention. It is thus noted that the humectant containing a polysaccharide obtained according to the present invention is superior to various humectant known types of sodium hyaluronate in that it is less susceptible to the change of relative humidity.

Example 8 (Evaluation of tyrosinase-inhibitory activity)

To 2.4 ml of a 0.1M phosphate buffer solution (pH 6.5), 0.1 ml of a 2,000 U/ml solution of mushroom-derived tyrosinase in a 0.05M phosphate buffer (pH 6.5) and 0.1 ml of a 300 μg/ml solution of the polysaccharide obtained in Example 2 in a 0.05M phosphate buffer (pH 6.5) were added, and then 0.4 ml of a 1.5 mM solution of L-tyrosine in a 0.05M phosphate buffer (pH 6.5) was further added to initiate the reaction and carry out incubation at 25° C. for 10 minutes. Absorbance at 475 nm was measured by an ultraviolet visible spectrophotometer. The above process was repeated without adding the polysaccharide, and the absorbance was measured in the similar way and given as blank.

The above process was further carried out using the polysaccharide obtained in Example 3. By way of comparison, the same process was also carried out using kojic acid (produced by Tokyo Kasei Kogyo KK). The tyrosinase inhibition rate was calculated from the following equation. The results are shown in Table 14 as relative values to the inhibition rate of kojic acid which is given as 1.0.

Tyrosinase inhibition rate=$(OD_2-OD_1)/OD_2 \times 100$ wherein $OD_1$ is absorbance at 475 nm in case the specimen was added, and $OD_2$ is absorbance at 475 nm in case no specimen was added (blank).

TABLE 14

| Material | Tyrosinase inhibition rate |
|---|---|
| Polysaccharide obtained in Example 2 | 0.2 |
| Polysaccharide obtained in Example 3 | 0.3 |
| Kojic acid | 1.0 |

As is seen from the above results, the polysaccharides used in the present invention are recognized to have a tyrosinase inhibitory activity although lower than that of kojic acid, and their use as a cosmetic adjunct is expected.

Example 9 (Preparation of polysaccharide-containing beauty wash)

A beauty wash was prepared from the formulation shown below. (1), (2), (5) and (6) were dissolved in (10) by heating, and then, after the solution restored room temperature, a mixed solution of (4), (8) and (9) in (7) was added slowly and solubilized in the first-said solution, followed by filtration of the resulting solution to obtain a beauty wash. A similar beauty wash was prepared likewise using the polysaccharide obtained in Example 3 in place of (1).

Formulation

| | |
|---|---|
| (1) Polysaccharide obtained in Example 2 | 0.5 wt % |
| (2) 1,3-Butylene glycol | 2.5 wt % |
| (3) Glycerol (86%) | 0.5 wt % |
| (4) Polyoxyethylene-hardened castor oil (40 E.O.) | 0.5 wt % |
| (5) Lactic acid | 0.05 wt % |
| (6) Sodium lactate | 0.7 wt % |
| (7) Ethanol | 7.0 wt % |
| (8) Methyl paraoxybenzoate | 0.1 wt % |
| (9) Perfume | 0.05 wt % |
| (10) Purified water | 88.1 wt % |

Example 10 (Preparation of polysaccharide-containing milky lotion)

A milky lotion was prepared from the formulation shown below. First, (1)–(8) and (12) were dissolved by heating, and the solution was maintained at 70° C. (oil phase). Then (9)–(11) were dissolved in (13) by heating, and this solution was added gradually to said oil phase and emulsified, followed by gradual cooling to prepare a milky lotion. A similar milky lotion was prepared likewise using the polysaccharide obtained in Example 3 in place of (11).

Formulation

| | |
|---|---|
| (1) Liquid paraffin | 4.0 wt % |
| (2) Squalane | 4.0 wt % |
| (3) Cetanol | 0.5 wt % |
| (4) Stearic acid | 1.5 wt % |
| (5) Sorbitan monooleate | 1.0 wt % |
| (6) Polyoxyethylene sorbitan monooleate (20 E.O.) | 1.0 wt % |
| (7) Glycerol monostearate | 0.5 wt % |
| (8) Ethyl paraoxybenzoate | 0.2 wt % |
| (9) Glycerol | 3.0 wt % |
| (10) 1,3-Butylene glycol | 5.0 wt % |
| (11) Polysaccharide obtained in Example 2 | 0.3 wt % |
| (12) Perfume | 0.05 wt % |
| (13) Purified water | 78.95 wt % |

Example 11 (Preparation of polysaccharide-containing cream)

A cream was prepared from the formulation shown below. First, (1)–(7) were dissolved in (11) under heating, and the solution was maintained at 70° C. (oil phase). Then (8)–(10) were dissolved in (12) by heating, and this solution was added gradually to said oil phase with stirring, followed by homomixer treatment and quick cooling to obtain a cream. A similar cream was prepared likewise using the polysaccharide obtained in Example 3 in place of (8).

Formulation

| | |
|---|---|
| (1) Vaseline | 8.0 wt % |
| (2) Lanoline | 2.0 wt % |
| (3) Squalane | 20.0 wt % |

-continued

| | |
|---|---|
| (4) Cetanol | 5.0 wt % |
| (5) Glycerol monostearate | 2.0 wt % |
| (6) Sorbitan polyoxyethylenemonolaurate (20 E.O.) | 2.0 wt % |
| (7) Ethyl paraoxybenzoate | 0.2 wt % |
| (8) Polysaccharide obtained in Example 2 | 0.5 wt % |
| (9) Glycerol (86%) | 5.0 wt % |
| (10) 1,3-Butylene glycol | 5.0 wt % |
| (11) Perfume | 0.1 wt % |
| (12) Purified water | 50.2 wt % |

Example 12 (Preparation of polysaccharide-containing pack)

A pack was prepared from the formulation shown below. (2), (3), (4) and (6) were added and dissolved in (8) by stirring, then (1) was added and dissolved by heating, and finally a solution of (5) in (7) was further added and dissolved to obtain a pack. A similar pack was also prepared likewise using the polysaccharide obtained in Example 3 in place of (4).
Formulation

| | |
|---|---|
| (1) Polyvinyl alcohol | 18.0 wt % |
| (2) Polyethylene glycol | 2.0 wt % |
| (3) 1,3-Butylene glycol | 5.0 wt % |
| (4) Polysaccharide obtained in Example 2 | 0.5 wt % |
| (5) Ethanol | 8.0 wt % |
| (6) Ethyl paraoxybenzoate | 0.1 wt % |
| (7) Perfume | 0.05 wt % |
| (8) Purified water | 66.35 wt % |

Example 13 (Preparation of polysaccharide-containing essence)

An essence was prepared from the formulation shown below. (1)–(8) were dissolved in (10) by heating, and then (9) was added and solubilized to obtain an essence. A similar essence was prepared likewise using the polysaccharide obtained in Example 3 in place of (1).
Formulation

| | |
|---|---|
| (1) Polysaccharide obtained in Example 2 | 1.5 wt % |
| (2) 1,3-Butylene glycol | 20.0 wt % |
| (3) Glycerol (86%) | 15.0 wt % |
| (4) Polyethylene glycol | 5.0 wt % |
| (5) Polyoxyethylene hexadecyl ether (20 E.O.) | 0.1 wt % |
| (6) Citric acid | 0.05 wt % |
| (7) Sodium citrate | 0.5 wt % |
| (8) Ethyl paraoxybenzoate | 0.2 wt % |
| (9) Perfume | 0.1 wt % |
| (10) Purified water | 58.05 wt % |

Example 14 (Evaluation of antistatic activity of polysaccharide-based antistatic agent)

A 1% (w/v) aqueous solution of the polysaccharide obtained in Example 2 was cast onto a glass-made Petri dish (90 mm in diameter and 10 mm high) and dried at 50° C. to form an approximately 30 $\mu$m thick film on the dish. After leaving the film under the conditions of 25° C. and 40% RH for 24 hours, the surface resistance of the film was measured by using a Digital Electrometer (Advantest Inc.) under the same temperature and humidity conditions and the surface resistance was determined. For the sake of, a similar film was formed using, instead of said polysaccharide, pullulan (produced by Hayashibara Biochemical Research Center Co., Ltd.) which is a commercially available microorganism-produced polysaccharide whose aqueous solution has low viscosity, easy to treat and useful as film-forming agent. The results are shown in Table 15. Measurement of surface resistivity is commonly adopted as a simple method of evaluation of antistatic activity. The lower the surface resistivity of a film, the higher is rated its antistatic activity.

TABLE 15

| Material | Surface resistivity ($\Omega$) |
|---|---|
| Polysaccharide obtained in Example 2 | $2.36 \times 10^8$ |
| Pullulan | $1.55 \times 10^{10}$ |
| Blank (water alone) | $1.60 \times 10^{12}$ |

Example 15 (Evaluation of antistatic activity of polysaccharide-based antistatic agent)

In 99 g of water, 0.1 g of the polysaccharide obtained in Example 2 was dissolved to prepare an aqueous solution of said polysaccharide. There were likewise prepared the aqueous solutions of pullulan (PF-20 (trade name) produced by Hayashibara Biochemical Research Center Co., Ltd.) and a hard type sodium dodecylbenzene-sulfonate salt (produced by Tayca Corp.). An aqueous solution of a soft type lithium dodecylbenzenesulfonate salt (produced by Tayca Corp.) was also prepared by using methanol in place of water.

Each of these solutions was dip coated on a high-quality paper to a dry coating weight of 2.0 g/m² and dried at 70° C. to produce an electroconductive sheet. Surface resistivity of the thus obtained four types of electroconductive sheet was measured under the conditions of 20° C. and 60% RH. The results are shown in Table 16.

TABLE 16

| Material | Surface resistivity ($\Omega$) |
|---|---|
| Polysaccharide obtained in Example 2 | $0.20 \times 10^{13}$ |
| Pullulan | $0.88 \times 10^{13}$ |
| Soft type lithium dodecylbenzenesulfonate salt | $0.24 \times 10^{13}$ |
| Hard type sodium dodecylbenzenesulfonate salt | $0.58 \times 10^{13}$ |

Example 16

In 88 g of purified water, 1.0 g of the polysaccharide obtained in Example 2 and 5.0 g of glycerol were dissolved by heating to prepare an aqueous solution of 70° C. Then 2.0 g of cetyl alcohol, 3.0 g of silicone oil and 1.0 g of polyoxyethylene (10 mol) oleylalcohol ether were mixed and dissolved by heating, and with temperature maintained at 70° C., the mixture was added to said aqueous solution by stirring well. The mixed solution was then cooled to room temperature with stirring continued to prepare a hair rinse.

Using the thus prepared rinse, the washed hair was rinsed and dried by a dryer. When the thus treated hair was brushed in a room air-conditioned to 20° C. and 30% RH, there took place no trouble due to static electricity such as clinging of hairs to the brush.

Example 17

In 50 ml of a 1% (w/v) aqueous solution of the polysaccharide obtained in Example 2, 50 ml of ethanol was mixed gradually and the obtained solution was put into a sprayer and sprayed to the lining (made of polyester) of a skirt at a rate of 2.5 g/m$^2$.

As a test, a woman wearing the thus treated skirt walk around in a room conditioned to 15° C. and 40% RH, there took place no electrostatic clinging of the skirt to her legs.

Example 18 (Evaluation of dispersibility of polysaccharide-based dispersant for inorganic substances)

There were prepared the 0.35% (w/v) aqueous solutions (60 g each) of the polysaccharides obtained in Examples 2 and 3 and xanthan gum (produced by Kelco Corp.). To each of said aqueous solutions and a sample composed of water alone, 40 g of titanium oxide (JR-701 (trade name) produced by Tayca Corp.) was added and mixed by stirring (at 5,000 r.p.m. for 5 minutes) with a homomixer to obtain uniform dispersion. The resultant slurry viscosity was measured by a B type viscometer (60 r.p.m., 25° C.). The results are shown in Table 17.

TABLE 17

| Material | Slurry viscosity (cps) |
|---|---|
| Polysaccharide obtained in Example 2 | 70 |
| Polysaccharide obtained in Example 3 | 10 |
| Xanthan gum | 710 |
| Water alone | 510 |

The evaluation of dispersibility by measuring viscosity of the dispersion is commonly practiced as a simple test method of ordinary pigment dispersants. In this case, the lower the viscosity of the dispersion, the better is rated the dispersibility of the dispersant.

As is seen from the above results, when using a dispersant comprising a polysaccharide obtained according to the present invention, the dispersed slurry shows a far lower value of viscosity than when using water alone for dispersion or when using xanthan gum known as a conventional polysaccharide dispersant, which indicates that the polysaccharides used in the present invention have sufficient dispersibility for titanium oxide. When said dispersed slurries were left still for 2 days and then their viscosity was measured in the same manner as described above, it was found that the slurries formed by using the polysaccharides prepared according to the present invention remained substantially unchanged in viscosity.

Thus, the dispersants provided according to the present invention can effectively be applied to the paints containing inorganic pigments such as titanium oxide.

Example 19 (Evaluation of dispersibility of polysaccharide based dispersant for inorganic substances)

There were prepared the 0.14%, 0.35% and 0.7% (w/v) aqueous solutions (60 g each) by using the polysaccharide obtained in Example 3, xanthan gum (Kelco Corp.) and pullulan (Hayashibara Biochemical Research Center Co., Ltd.). Titanium oxide was dispersed in each of these aqueous solutions to form a slurry and its viscosity was measured in the same manner as in Example 18. The results are shown in Table 18.

TABLE 18

| Solution concentration (w/v %) | 0.14 | 0.35 | 0.7 |
|---|---|---|---|
| Material | Slurry viscosity (cps) | | |
| Polysaccharide obtained in Example 3 | 400 | 10 | 20 |
| Xanthan gum | 710 | 710 | 1450 |
| Pullulan | 580 | 540 | 320 |

As is seen from the above results, the polysaccharide used in the present invention shows excellent dispersibility in various concentrations, even in a low range.

Example 20 (Evaluation of dispersibility of polysaccharide-based dispersant for inorganic substances)

Slurries were formed by the same procedure as in Example 18 except that 30 g of slaked lime was added to 60 g of a 0.2% (w/v) aqueous solution, and their viscosity was measured. The results are shown in Table 19.

TABLE 19

| Material | Slurry viscosity (cps) |
|---|---|
| Polysaccharide obtained in Example 2 | 30 |
| Polysaccharide obtained in Example 3 | 50 |
| Xanthan gum | 600 |
| Water alone | 400 |

As is seen from the above results, the polysaccharides used in the present invention have enough dispersibility for slaked lime. Therefore, the dispersant using a polysaccharide according to the present invention can be applied to manufacture of artificial bones and teeth.

Example 21 (Evaluation of dispersibility of polysaccharide-based dispersant for inorganic substances)

Slurries were prepared by the same procedure as in Example 18 except that 50 g of Portland cement was added to 25 g of a 1% (w/v) aqueous solution of polysaccharide, and the slurry viscosity was measured in the same way as in Example 18. The results are shown in Table 20.

TABLE 20

| Material | Slurry viscosity (cps) |
|---|---|
| Polysaccharide obtained in Example 2 | 500 |
| Polysaccharide obtained in Example 3 | 360 |
| Xanthan gum | >10,000 (clayey) |
| Water alone | 800 |

As is seen from the above results, the polysaccharides used in the present invention have satisfactory dispersibility for Portland cement, and the dispersant comprising a polysaccharide according to the present invention is practically usable as a dispersant or water-reducing agent for cement.

Example 22 (Evaluation of dispersibility of polysaccharide-based dispersant for inorganic substances)

There were prepared the 0.14% (w/v) aqueous solutions (60 g each) of the polysaccharides obtained in Examples 2 and 3 and xanthan gum (Kelco Corp.). Then, following the procedure of Example 20, slurries were prepared by adding 42 g of talc or kaolin to said aqueous solutions and a sample composed of water alone, and their viscosity was measured. The results are shown in Table 21.

TABLE 21

| Type of inorganic powder | Polysaccharide obtained in Example 2 | Polysaccharide obtained in Example 3 | Xanthan gum | Water alone |
|---|---|---|---|---|
| | | Slurry viscosity (cps) | | |
| Talc | 65 | 50 | 200 | 250 |
| Kaolin | 200 | 510 | 340 | 800 |

As is seen from the above results, the polysaccharides used in the present invention have satisfactory dispersibility for the pigments which are usually flaky, and the dispersant comprising a polysaccharide according to the present invention is practically usable in the field of coating materials and ceramics.

Example 23 (Evaluation of dispersibility of polysaccharide-based dispersant for inorganic substances)

Slurries were prepared and their viscosity was measured by the same procedure as in Example 22 except that clay or barium sulfate was added to a 0.7% (w/v) aqueous solution of polysaccharide. The results are shown in Table 22.

TABLE 22

| Type of inorganic powder | Polysaccharide obtained in Example 2 | Polysaccharide obtained in Example 3 | Xanthan gum | Water alone |
|---|---|---|---|---|
| | | Slurry viscosity (cps) | | |
| Clay | 9000 | 6700 | >10000 (clayey) | >10000 |
| Barium sulfate | 1000 | 850 | 1800 (gel-like) | 4100 |

As is seen from the results of Examples 18–23 it is expected that the dispersant of the present invention can be used in many fields of industrial materials including paints, medical and dental materials, contrast medium, structural and ceramic materials and the like.

Example 24 (Evaluation of dispersibility of polysaccharide-based dispersant for oleaginous substances)

To the 2% (w/v) aqueous solutions (30 g each) of the polysaccharides obtained in Examples 2 and 3, 30 g each of liquid paraffin, squalane, vaseline, lanoline and salad oil were added severally as oleaginous components and mixed by stirring with a homomixer (10,000 r.p.m., 5 minutes). The thus prepared 5 types of mixed solutions were allowed to stand at 50° C. for 10 days, but there took place no separation of water and oil phases.

Example 25 (Evaluation of dispersibility of polysaccharide-based dispersant for oleaginous substances)

Mixed solutions were prepared by combining 30 g each of the 2% (w/v) aqueous solutions of the polysaccharides obtained in Examples 2 and 3, water and liquid paraffin in the same manner as in Example 24, and the average particle size of the emulsion just after the mixing and that after 10-day standing at 50° C. were measured for each mixed solution. A laser diffraction type particle size distribution meter (Model SALD-1100 mfd. by Shimadzu Corp.) was used for measuring the average particle size. The results are shown in Table 23.

TABLE 23

| | Average particle size of emulsion ($\mu$m) | |
|---|---|---|
| Material | Immediately after mixing | After 10-day standing at 50° C. |
| Polysaccharide obtained in Example 2 | 5 | 5 |
| Polysaccharide obtained in Example 3 | 4 | 4 |
| Xanthan gum | 136 | 169 |
| Pullulan | Unmeasurable | Unmeasurable |
| Water alone | Unmeasurable | Unmeasurable |

(In case pullulan or water alone was used, there took place separation of the water and oil phases immediately after the end of mixing, so that it was impossible to measure the average particle size of the emulsion.)

As is seen from the results of Examples 24 and 25, the polysaccharides used in the present invention can form a fine and stable emulsion with the oleaginous substances. Therefore, it is expected that the dispersant comprising such a polysaccharide according to the present invention can be used in the fields of cosmetics, foods, medicines and the like.

Example 26 (Measurement of viscosity of polysaccharide solutions)

There were prepared the 1% (w/v) aqueous solutions of the polysaccharides obtained in Examples 2 and 3 and the commercially available polysaccharides pullulan (supplied from Hayashibara Biochemical Research Center Co., Ltd.), xanthan gum (supplied from Kelco Corp.) and hyaluronic acid (supplied from Kibun Food Chemifa Co., Ltd.), and the viscosities of these aqueous solutions were measured by a B type viscometer (60 r.p.m., 25° C.). The results are shown in Table 24.

TABLE 24

| Material | Viscosity of 1% (w/v) aqueous solution (cps) |
|---|---|
| Polysaccharide obtained in Example 2 | 20 |
| Polysaccharide obtained in Example 3 | 10 |
| Pullulan | 10 |
| Xanthan gum | 1,470 |
| Hyaluronic acid | 5,800 |

As is seen from the above results, the viscosity of the aqueous solutions of the polysaccharides used in the present invention is almost equal to that of pullulan and far lower than those of xanthan gum and hyaluronic acid. Therefore, it is easy with the film-forming agent of this invention to prepare a high-concentration solution, and the films can be made at high efficiency by using said film-forming agent.

Example 27 (Preparation of films and evaluation thereof)

The 2% (w/v) aqueous solutions of the polysaccharides obtained in Examples 2 and 3 and pullulan (supplied from Hayashibara Biochemical Research Center Co., Ltd.) were prepared. Each solution was cast into a template (50×50×1 mm) placed on a PET sheet and dried at 50° C. to prepare a film. Tensile strength and break elongation of the produced films were measured by a precision universal tester (AGS-500B mfd. by Shimazdu Corp.) according to JIS Z 1707. The results are shown in Table 25.

TABLE 25

| Material | Tensile strength (kg/cm²) | Break elongation (%) |
|---|---|---|
| Polysaccharide obtained in Example 2 | 700 | 9 |
| Polysaccharide obtained in Example 3 | 500 | 6 |
| Pullulan | 500 | 3 |

As is seen from the above results, the films made by using the film-forming agent of the present invention are equal to or higher than the pullulan film in tensile strength and excel the pullulan film in break elongation.

Example 28 (Detergent pack)

On a film (10×20 cm) made in the same way as in Example 27 by using the polysaccharide obtained in Example 2, 30 g of a commercially available powdered detergent for clothing was placed, then another film of the same size was placed thereon and its periphery was heat sealed to make a detergent pack.

This detergent pack was put into the 40-liter water tank of an automatic washer containing laundry, and the washer was operated to send water into the tank, whereupon the film was dissolved away and the detergent contained in the pack spread out in the water tank.

If a detergent is packed by using the film of the present invention to make a detergent pack as described above, it is possible to save the trouble of weighing the detergent and to prevent scatter of the detergent which could occur during weighing or feeding of the detergent when it is treated in the form of powder.

Example 29 (Agricultural chemical pack)

On a film (10×20 cm) prepared in the same manner as in Example 27 by using the polysaccharide obtained in Example 2, 10 g of an insecticide 1-naphthyl-N-methyl carbamate (NAC) was placed, then another film of the same size was placed thereon and its periphery was heat sealed to prepare an agricultural chemical pack.

When this pack was thrown into a puddy field, the film was dissolved away and NAC contained in the pack was released into the puddy field.

If an agricultural chemical compound is packed by using the film of the present invention as described above, the compound can be treated without direct touch with the user's hands. This is quite desirable from the hygienic standpoint.

Example 30 (Preparation of cosmetic pack)

A cosmetic pack was prepared from the formulation shown below. (1), (2), (3) and (4) were dissolved in (7) by stirring, and then (6) in which (5) has been dissolved was added and dissolved to obtain a cosmetic pack.

Formulation

| | |
|---|---|
| (1) Polyethylene glycol | 2.0 wt % |
| (2) 1,3-Butylene glycol | 5.0 wt % |
| (3) Polysaccharide obtained in Example 2 | 18.5 wt % |
| (4) Sodium paraoxybenzoate | 0.1 wt % |
| (5) Perfume | 0.05 wt % |
| (6) Ethanol | 8.0 wt % |
| (7) Purified water | 66.35 wt % |

Example 31 (Preparation of microbial infection preventive and remedial agent)

To 500 ml of a 1% (w/v) aqueous solution of the polysaccharide obtained in Example 2 was added 3 g of zinc sulfate ($ZnSO_4 \cdot 7H_2O$) with stirring. Then the solution was desalted by ultrafiltration and freeze-dried to obtain a polysaccharide in which the counter ion of the uronic acid residue was zinc ion. Using this polysaccharide, a film was prepared in the same manner as in Example 27.

By attaching this film to the region of wound, it is possible to prevent infection by germs while healing the wound.

Example 32 (Preparation of instant juice film)

In 180 ml of water having dissolved therein 10 g of a commercial powdered juice, the polysaccharide obtained in Example 3 was dissolved by heating to a concentration of 30% w/v). Using this solution, a film was prepared by the same procedure of Example 27. When this film was put into 180 ml of water and stirred with a stick, the film was dissolved in water to form juice.

By forming powdered juice into a film in the manner described above, it is possible to save the trouble of weighing the powder when it is dissolved in water to make juice.

What is claimed is:

1. A method of using a polysaccharide composed of D-glucuronic acid, L-rhamnose, D-galactose and D-glucose in a molar ratio of D-glucuronic acid:L-rhamnose:D-galactose:D-glucose=0.8–1.2:2.4–3.6:0.8–1.2:0.8–1.2, for producing a humectant, antistatic agent, film-forming agent or dispersant, wherein the bonding pattern and the molar ratio of constituent sugar residues of the polysaccharide are as follows:

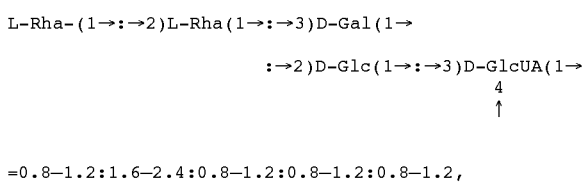

=0.8-1.2:1.6-2.4:0.8-1.2:0.8-1.2, wherein Rha, Gal, Glc and GlcUA represent rhamnose residue, galactose residue, glucose residue and glucuronic acid residue, respectively, and the numerals indicate the position of glucoside bond; said method comprising culturing a polysaccharide-productive *Kliebsiella oxytoca* TNM-3 strain (FERM BP-4669), Kliebsiella K-19 strain or mutant thereof under conditions suitable for producing the polysaccharide, collecting the polysaccharide from the culture, and using an effective amount of the polysaccharide for producing the humectant, antistatic agent, film-forming agent or dispersant.

2. A method according to claim 1, wherein the molecular weight of the polysaccharide measured by gel permeation chromatography is approximately $1 \times 10^3$ to $10 \times 10^6$.

3. A method for producing a humectant, antistatic agent, film-forming agent or dispersant, comprising culturing a polysaccharide-productive *Klebsiella oxytoca* TNM-3 strain (FERM BP-4669), Klebsiella K-19 strain or mutant thereof under conditions suitable for producing the polysaccharide, collecting from the culture a polysaccharide composed of D-glucuronic acid, L-rhamnnose, D-galactose and D-glucose in a molar ratio of D-glucuronic acid:L-rhamnose:D-galactose:D-glucose= 0.8–1.2:2.4–3.6:0.8–1.2:0.8–1.2, and using an effective amount of the polysaccharide for producing the humectant, antistatic agent, film-forming agent or dispersant.

4. A biologically pure culture of a polysaccharide-productive *Klebsiella oxytoca* TNM-3 strain (FERM BP-4669), or mutants thereof having all the identifying characteristics of said strain.

* * * * *